United States Patent [19]
Perreault et al.

[11] Patent Number: 6,150,096
[45] Date of Patent: Nov. 21, 2000

[54] MOLECULAR MARKERS FOR THE DIAGNOSIS OF HUMAN DISEASES INCLUDING CROHN'S DISEASE

[75] Inventors: Jean-Pierre Perreault, Fleurimont; Daniel LaFontaine, St.-Alexis-de-Montcalm; Stéphane Mercure, Sherbrooke, all of Canada

[73] Assignee: Universite de Sherbrooke, Sherbrooke, Canada

[21] Appl. No.: 08/938,783

[22] Filed: Sep. 26, 1997

[51] Int. Cl.$^7$ ............................ C12Q 1/68; C07H 21/04
[52] U.S. Cl. ..................... 435/6; 536/23.5; 536/24.33
[58] Field of Search ................. 435/6, 91.2, 91.51; 536/24.33, 24.3; 935/8, 17, 77, 78

[56] References Cited

U.S. PATENT DOCUMENTS 5,487,985  1/1996  McClelland et al. .............. 435/91.2
5,665,547  9/1997  Pardee et al. ..................... 435/6

OTHER PUBLICATIONS

LaFontaine et al. Medecine Sciences 11 (Suppl.2) 21, Abstract #74, 1995.
Ruef et al. Mol. and Biochem Parasitology 62 117–120, Nov. 1993.
Iltzsch et al. J. Biol. Chem. 267: 14504–14508,Jul. 1992.
Preston et al. Mol. Cell. Biol. 11:5801–5812, Dec. 1991.
Gen Bank Accession No. U17999 as reported in Friedman et al. Cancer Res. 54:6374:6382, Apr. 1996.
Ricote et al. Mutation Research 374:153–167, Mar. 1997.
Soutar et al. Br. J. Haematol. 97:247–248, Apr. 1997.
Sokolov et al. Nucl. Acids Res 22:4009–4015, Sep. 1994.
Ercolani et al. J. Biol. Chem. 263:15335–15341, Oct. 1988.
Zhao et al. Gene 155:159–165, Apr. 1995.
Perucho et al. Meth. Enzymol. 254:275–290, 1995.
Welsh et al. Nucl. Acids Res 18:7213–7218, Dec. 1990.
Welsh et al. Nucl. Acids Res 20:4965–4970, Oct. 1992.
Diachenko et al. Biochem. Biophys. Res. Comm., 219:824–828, Feb. 1996.
McLaughlan et al. J. Pathol. 181:87–92, Jan. 1997.
Liang P et al., Science, 1992; 257:967–71.
McClelland M et al., *Trends in Genetic*, 1995; 11:242–46.
Welsh J et al., DNA and RNA fingerprinting using arbitrarily primed PCR. In: Sninski JJ et al., ed. *PCR Protocols*, 2nd edition, San Diego, Acad. Press, 1994.
Chomczynski P et al., *Anal. Biochem.*, 1987; 162:156–159.
Isaacs KL et al., *Gastroenterology 1992*; 103:1587–95.
Reimund J–M et al., *Gut 1996*; 39:684–89.
Sambrook J et al., Analysis of RNA. In: *Molecular cloning–A laboratory manual*, 2nd ed. Cold Spring Harbor, Cold Spring Harbor Lab. Press, 1989: 7.37–7.52.
Altschul SF et al., *J. Mol. Biol. 1990*; 215:403–410.

*Primary Examiner*—Lisa B. Arthur
*Assistant Examiner*—Jehanne Souaya
*Attorney, Agent, or Firm*—Swabey Ogilvy Renault; Kevin P. Murphy

[57] ABSTRACT

The present invention relates to an arbitrarily primed PCR-based method to identify genetic marker associated with a pathology, which comprises the steps of: a) collecting heterogeneous nucleic acid samples from diseased and healthy tissues; b) determining quantities of the nucleic acid pools by specific amplification of a fragment of glyceraldehyde-phosphate dehydrogenase (GAPDH) mRNA; c) amplifying nucleic acid pools of step b) using non-specific sense and antisense primers to obtain clear patterns of nucleic acid sequences; and d) subjecting amplified nucleic acid sequences to gel electrophoresis to obtain fingerprints of both diseased and healthy, wherein bands predominantly associated with diseased tissues are markers for the pathology. The present invention also relates to a RNA expression marker for the diagnosis of Crohn's disease, which comprises a 3.1 kb RNA sequence, and uses thereof.

2 Claims, 3 Drawing Sheets

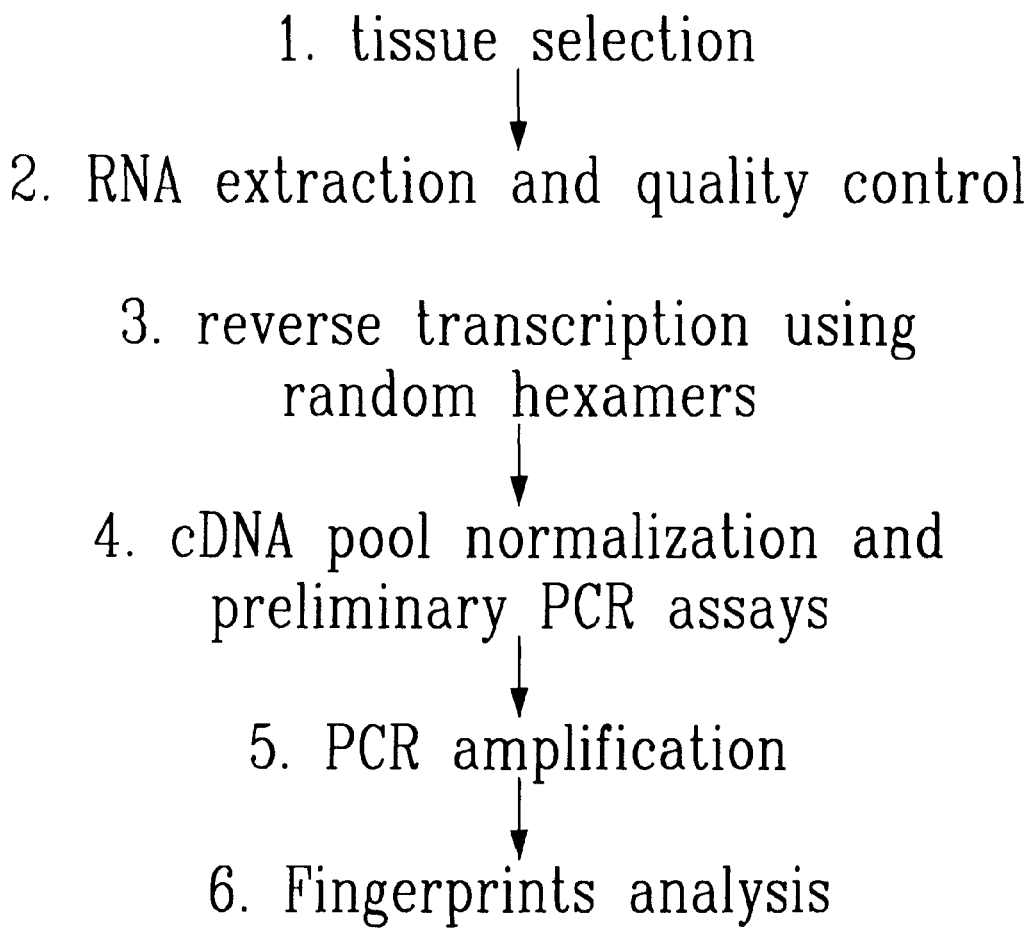

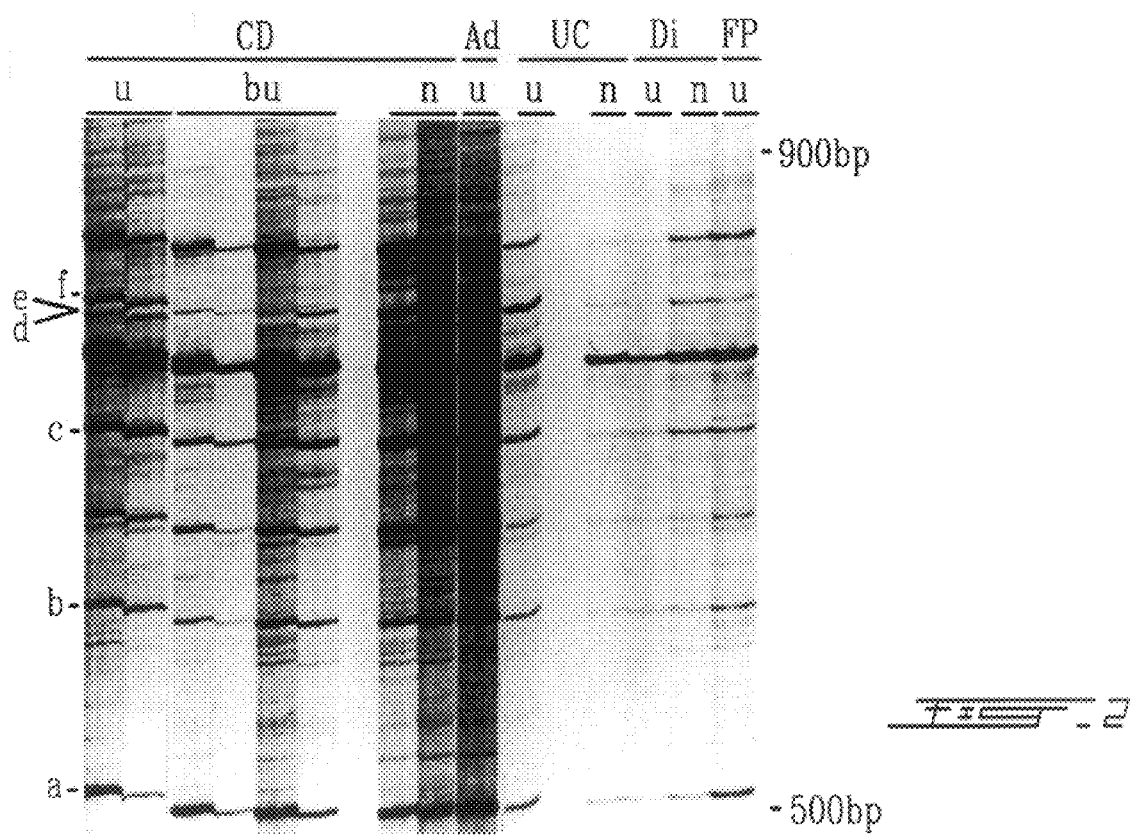

```
   1 GCTTTTCCT TCCCCTTGT AAAGTCTAAG ACAAAAACTC ACACCTGGAC
  51 CAGGCTGACT CCTGGTGTAA AGCAGGAAGA TGTGATGAAA ACTAGAGCCA
 101 GCAATGTCAG CTGGCACTTT AGTCTGGGAT GCTGTGTGG TCAGTTTCGC
 151 CTACAGAACC CCAAAGAAAT TACACTGAGG GGTACGTCTG ACCCCTTTCC
 201 GGAGTCCCA GGGTCACGGG GCAGAAACTT CTCTCCACA CACCAAGCCC
 251 CAGGCCAGGG CCCTGGGAAA CCTCCCATGT CCTCGTCCCA CCTGCCCCAT
 301 GTGGTTGTAC TGTTTCTCCC ATATTAGAGA TGTACAGAAC CAAGACTCAG
 351 ACAAGCGAAA TGCATCCAAT CCAAAGGCAC AGAAATGATG GTGGAGATGC
 401 AAGTGCTGCA TCCAGGTCTA GCTGACTCAA AGCCCATGG CTTTTTCTA
 451 CTGTTTCTTT CTGCACTTCA CCAAAATTGG GAGACTCCTG GTGATGGCAA
 501 GCTGACTGTC TCCTGCGGCG TTTTCATTGC GTCTGTCAAG TTTCATTTCA
 551 GGGGATAGGG ATCGAGCAGC ACAGATTCGA AACTTCCAA ATCTCCAATA
 601 AAAACAGACA GAACAATGAG AAGGCAAAAC TAAACCCTTT AGACAACCTC
 651 TACAGTCAAAT GAGGTGACAA CGTGTCCCCA AACTACAAAT ACAATCAGGT
 701 GGGTGGAGGG CACCAAATAC AAGTAACTGT GTGTCACCAG CATCTGTGTA
 751 TGGTCAGAGCA AGGGAAGCTC CGGGCTCTGG CAGGCTGGAG ATCAGGGAAC
 801 AGTAAGCTAG CCAACAGATG CTCAGAGGCA AACATGACAA ACCACAGGAC
 851 TGTGTCAGAA GCTGAGAGGCA GTTCTAACT AAAAGCATGT GATGTCAAGA
 901 AGTCTAGTCT AGGGTAGGCT GACCTCCATA GATTCTCCAG AATGAATGTC
 951 CAGGGCTTTC TTCCAGCAGG GCCCCTTGCTG ACAGCAGATT CAACACTGAG
1001 ACAAGAGGGA TGACAGCAGC AAAGAAGAGT GGACCAGATA ACAGGAGGAC
1051 GGGGAAGGAA ACAGG
```

FIG. 3A

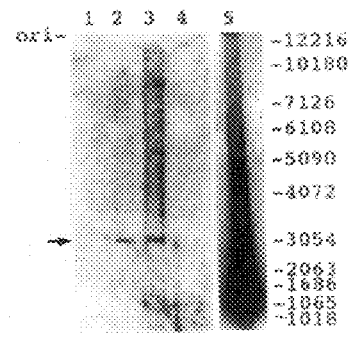

FIG. 3B

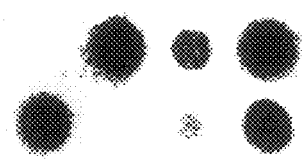

FIG. 3C

MOLECULAR MARKERS FOR THE DIAGNOSIS OF HUMAN DISEASES INCLUDING CROHN'S DISEASE

BACKGROUND OF THE INVENTION (a) Field of the Invention

The invention relates to molecular markers for the diagnostic of human diseases such as Crohn's disease (CD).

(b) Description of Prior Art

Crohn's disease (CD) is a chronic inflammatory bowel disease (IBD) that can develop anywhere along the gastrointestinal tract. Its etiology is unknown; however, CD is believed to be due to a combination of factors involving diet, genetic background, immunologic responses, and the environment.

In tissues affected by IBD, namely CD and ulcerative colitis (UC), several genes have been shown to be differentially expressed. For example: (i) the expression of mRNA for interleukin-1 (IL-1) and IL-1ra differs in colonic biopsy specimens between IBD patients and inflammatory controls from patients with acute colitis (Isaacs KL et al., *Gastroenterology*, 1992; 103:1587–95); and, (ii) tumor necrosis factor a (TNF-α), IL-1B and IL-6 have all been shown to be overexpressed in the inflamed areas of CD specimens as compared to both normal areas and other IBD controls (Reimund J-M et al., *Gut* 1996; 39:684–89). These genes are all related to the immunological response leading to the inflammation. However, neither the presence of these mRNAs, nor that of their respective proteins, appears useful as specific markers to unequivocally distinguish CD affected tissues from other intestinal diseases.

An important need for the modern medical diagnosis is the development of a clinical molecular marker that positively discriminates a pathology from others. Within this context, the primary aim has been to identify differences in the genetic expression patterns of healthy and diseased tissues. To date, RNA fingerprinting (e.g. differential display and RNA arbitrarily primed PCR such as RAP-PCR) using reverse transcriptase coupled to the polymerase chain reaction (RT-PCR) appears to be the most promising approach for the identification of such molecular markers (Liang P et al., Science, 1992; 257:967–71; McClelland M et al., *Trends in Genetic,* 1995; 11:242–46; Welsh J et al., DNA and RNA fingerprinting using arbitrarily primed PCR. In: Sninski JJ et al., ed. *PCR Protocols,* 2nd edition, San Diego, Academic Press, 1994). RNA fingerprinting methods are semi-quantitative and can be used to scan RNA populations for differentially regulated genes based on their relative abundance. Both of these methods have been successful on many occasions, primarily when using RNA isolated from either bacterial or cell cultures that are relatively homogeneous populations. However, several groups working on the characterization of the gene expression associated with clinically important pathologies have been unable to develop any molecular markers using current RNA fingerprint methods. Two causes of these failures are the high heterogeneity of the RNA samples obtained when working with tissues, and the bias introduced by using a minimum number of specimens (e.g. only one diseased and one healthy sample).

It would be highly desirable to be provided with an arbitrarily primed PCR-based procedure designed to identify genetic expression differences between diseased and healthy human tissues using heterogeneous RNA samples.

Also it would be highly desirable to be provided with a marker for the diagnostic of Crohn's disease (CD).

SUMMARY OF THE INVENTION

One aim of the present invention is to provide an arbitrarily primed PCR-based procedure designed to identify genetic expression differences between diseased and healthy human tissues using heterogeneous RNA samples.

Another aim of the present invention is to provide with a marker for the diagnostic of Crohn's disease.

In accordance with the present invention, we refined the RAP-PCR procedure to help identify clinical markers when working with heterogeneous RNA population. Thus, we report the finding of cellular transcript that positively identifies CD affected tissues, therefore, having potential as CD diagnostic tool.

We propose to use both the appropriate pathological controls, and RNA from several samples of the target disease, in order to circumvent the heterogeneity problem. Also, we have added several control points to insure both the quality and quantity of the samples.

In accordance with the present invention there is provided an arbitrarily primed PCR-based method to identify genetic marker associated with a pathology, which comprises the steps of:

a) collecting heterogeneous nucleic acid samples from diseased and healthy tissues;

b) determining quantities of the nucleic acid pools by specific amplification of a fragment of glyceraldehyde-phosphate dehydrogenase (GAPDH) mRNA;

c) amplifying nucleic acid pools of step b) using non-specific sense and antisense primers to obtain clear patterns of nucleic acid sequences; and d) subjecting amplified nucleic acid sequences to gel electrophoresis to obtain fingerprints of both diseased and healthy, wherein bands predominantly associated with diseased tissues are markers for the pathology.

The nucleic acid samples may be DNA or RNA, with the proviso that the method using RNA samples further comprises a step I) before step b):

i) subjecting the RNA samples to reverse transcription using random hexamers primers to obtain cDNA pools.

Preferably, the fragment of GAPDH is a 487 bp fragment.

Preferably, the sense and antisense primers of step c) are each 5'GCTGTTTCCTTCCCCGTC 3' (SEQ ID NO:1).

In accordance with the method of the present invention, when the pathology is Crohn's disease, the marker may be a 3.1 kb RNA sequence as partly set forth in FIG. 3A (SEQ ID NO:2).

In accordance with the present invention there is also provided a RNA expression marker for the diagnosis of Crohn's disease, which comprises a 3.1 kb RNA sequence as partly set forth in FIG. 3A.

In accordance with the present invention there is also provided a method to obtain probes specific for the diagnosis of Crohn's disease; which comprises using the marker as partly set forth in FIG. 3A to identify specific probes.

In accordance with the present invention there is also provided a specific probe for the diagnosis of Crohn's disease which comprises a 1065 bp RNA sequence as set forth in FIG. 3A.

In accordance with the present invention there is also provided specific PCR primers for the diagnosis of Crohn's disease which comprises any primers complementary to a 5' and a 3' segment of the 3.1 kb RNA marker of the present invention.

In accordance with the present invention there is also provided an antibody specific for the immunodiagnosis of Crohn's disease, which comprises an antibody specifically raised against the 3.1 kb RNA marker of the present invention or a protein translated from the 3.1 kb RNA marker of the present invention.

In accordance with the present invention there is also provided method for the diagnosis of Crohn's disease in a patient; which comprises the steps of:

a) obtaining a biological sample of the patient; and b) subjecting the sample to at least one of the following to determine the presence of Crohn's disease marker:

i) a probe according to the present invention for a time sufficient for hybridization to occur with a complementary sequence potentially present in the sample;

ii) amplification of DNA of the sample using PCR primers of the present inventions; or iii) immunodetecting the marker using the anti-body of the present invention;

wherein a positive result in step b) is indicative of Crohn's disease.

BRIEF DESCRIPTION OF THE DRAWINGS

FIG. 1 illustrates the methodology of the procedure;

FIG. 2 illustrates an example of an autoradiogram obtained from AP-PCR;

FIG. 3A illustrates the characterization of the RNA species (SEQ ID NO:2);

FIG. 3B illustrates a Northern blot hybridization; and

FIG. 3C illustrates an example of a dot-blot hybridization assay.

DETAILED DESCRIPTION OF THE INVENTION

In accordance with the present invention, there is provided an arbitrarily primed PCR-based procedure designed to identify genetic expression differences between diseased and healthy human tissues. RNA fingerprinting methods (e.g. differential display and RAP-PCR) are semi quantitative and can be used to analyze RNA populations for differentially regulated genes (Liang P et al., Science, 1992; 257:967–71; McClelland M et al., Trends in Genetic, 1995; 11:242–46). Both of these methods have been successful on many occasions, primarily when using RNA isolated from relatively homogeneous populations like bacterial or cell cultures (Welsh J et al., DNA and RNA fingerprinting using arbitrarily primed PCR. In: Sninski JJ et al., ed. *PCR Protocols*, 2nd edition, San Diego, Academic Press, 1994). However, several groups working on the characterization of the gene expression associated with clinically important pathologies have been unable to identify molecular markers using current RNA fingerprint methods. Two causes of these failures are the high heterogeneity of the RNA samples obtained when working with tissues, and the bias introduced by using a minimum number of specimens (e.g. only one diseased and one healthy sample). To circumvent the problem of RNA heterogeneity we added a cDNA pool normalization step as well as several control points to insure both the quality and quantity of the samples (see Methods).

The strategy is summarized in FIG. 1.

Step 1: Sample selection:

The selection of appropriate surgical tissues or biopsies is a critical step. Selection should allow for the identification of RNA markers unique to a particular pathology, and should remove any marker(s) associated with a specific individual. Therefore, we propose to consider several appropriate control pathological specimens and several tissues of the pathology of interest. For example, we are currently interested in inflammatory bowel diseases (IBD), specifically both Crohn's disease and ulcerative colitis. These pathologies are two idiopathic, nonspecific inflammations that occur along the gastrointestinal tract. If the goal is a marker for the ulcerated areas associated with Crohn's disease (CD), tissues affected by adenocarcinoma are appropriate as cellular proliferation controls, while tissues affected by diverticulitis, familial polyposis or ulcerative colitis (UC) are appropriate as intestinal inflammation controls.

Step 2: RNA extraction:

After surgery, small sections from the ulcerated, the border of the ulcerated, and nearby visually normal tissues were isolated and rapidly snap-frozen and stored at −70° C. Total RNA from all three kinds of tissues was then extracted using the guanidinium thiocyanate method (TRIZOL™ reagent, Gibco BRL) (Chomczynski P et al., *Anal. Biochem.*, 1987; 162:156–159). The RNA was quantified by UV spectroscopy, and its quality verified by 1% agarose gel electrophoresis. Degraded RNA samples, probably due to extensive tissue necrosis, were rejected.

Step 3: RT reactions:

RT reactions were performed using random hexamers as primers. In theory, these primers will allow all (or most) of the RNA molecules to be represented in the resulting cDNA pool. In addition, the use of random hexamers offers the advantage that a single cDNA pool will be sufficient to perform all subsequent steps, regardless of the arbitrary primer used in the PCR assay, and thereby permit comparison of the different expression patterns for that sample. Prior to the RT, 1 $\mu$g of RNA was incubated in a volume of 10 $\mu$L for 10 minutes at room temperature with DNase I as recommended by the manufacturer (amplification grade, Gibco BRL). The primers (10 $\mu$L of 6.6 $\mu$M) were then annealed to the RNA by successive incubations at 70° C. and on ice for 10 minutes and 5 minutes, respectively. Reverse transcription reactions were performed with a modified form of moloney murine leukemia virus enzyme following the recommended protocol (Superscript II RNase H-, Gibco BRL), and the resulting samples stored at −20° C.

Step 4: Preliminary PCR:

Two types of preliminary PCR amplifications were performed. (i) The quantities of the various cDNA pools were normalized by the specific amplification of a 497 bp fragment of the glyceraldehyde-phosphate dehydrogenase (GAPDH) mRNA using 3 $\mu$L of the cDNA samples as template. Preliminary experiments have allowed us to establish the linear portion of the amplification curve under the conditions used. After this amplification, the volume of the various cDNA pools required to give the equivalent amounts of the 497 bp fragment are determined and used in all subsequent amplifications. (ii) In order to select the PCR primers with the greatest potential in our primer bank we performed preliminary assays using 2 or 3 RNA samples extracted from different tissues. Preference was given to primers that yielded clear patterns containing 100 to 200 bands ranging in size from 100 to 2000 bases. These amplifications were performed in accordance with the following conditions.

Only the section of the gel corresponding to fragments of 500 to 900 bases in length is shown in FIG. 2. The arbitrarily chosen primer, which served as both sense and antisense primer, had the sequence 5'GCTGTTTCCTTCCCCGTC 3' (SEQ. ID NO: 1) (annealing temperature estimated as 51.7° C.). An aliquot from the cDNA pool was added to the PCR reaction mixture in a final volume of 100 $\mu$L containing 10 mM Tris-HCl pH 8.3, 2.0 mM $MgCl_2$, 50 mM KCl, 0.2 mM dGTP, 0.2 mM dCTP, 0.2 mM dTTP, 1 µM DATP and 1 µM primer. The reaction mixtures were preincubated for 2 minutes at 94° C., then 1.5 units of Taq DNA polymerase (Pharmacia Biotech) was added, while maintaining this temperature, and two initial cycles of selection (successive incubations of 1 minute at 94° C., 2 minutes at 37° C., slow increase of 2° C./min. up to 72° C., 2 minutes at 72° C.) were performed. Finally, 20 µCi [α35S]dATP were added to the mixture and 28 amplification cycles (1 minute at 94° C., 2 minutes at 60° C. and 2 minutes at 72° C.) were performed. CD, UC, Ad, Di and FP indicate respectively Crohn's disease, ulcerative colitis, adenocarcinoma, diverticulitis and familial polyposis. RNA samples were extracted from ulcerated, the border of the ulceration, or normal areas are represented by u, bu, and n. The letters a–f indicate bands discussed in the text.

Step 5: AP-PCR:

The AP-PCR amplification is performed according to the conditions described above. The initial two cycles employed a 37° C. annealing temperature followed by a slow (2° C./min.) increase to 72° C. so as to favor elongation of partially annealed primers. The subsequent 28 cycles utilized a stringent annealing temperature (>50° C.), and were performed in the presence of [α35S]dATP. After the PCR amplification, the mixtures were phenol-chloroform extracted, isopropanol precipitated, ethanol washed and dried. The resulting pellets were resuspended in ~10 µL of loading buffer (0.3% each of bromophenol blue and xylene cyanol, 10 mM EDTA, pH 7.5, 97,5% deionized formamide), and 3 µL aliquots heat-denatured (90° C. for 1 minute and ice snap-cooled for 5 minutes) and electrophoresed on a 5% Long Ranger (J. T. Baker) sequencing gel (4 mm X 20 cm X 60 cm) (FIG. 2).

Step 6: analysis:

The dried gels were quantified using a PhosphorImager™ (Molecular Dynamics). Alternatively, the procedure was performed in order to analyze the RAP-PCR products by 1% agarose gel electrophoresis. As illustrated in FIG. 2 for AP-PCR performed in presence of radioactive DATP, the preliminary steps taken to minimize the various RNA populations were not enough to yield uniform fingerprints, although we observed that these procedures were essential for a rigorous analysis. The inclusion of several different samples, in addition to the use of long fingerprint gels, mandated that computer assisted analysis be an essential step in the procedure. The digitalized patterns were normalized for their intensity using two or three bands common to all samples (for example see bands d–f in FIG. 2). The genetic patterns obtained from specimens with the same condition were than superimposed in order to derive the mean expression pattern for each pathologic state. Finally, the mean expression patterns were compared, and the band (s) specific to one pathological condition identified. For example, samples from ulcerated areas of intestine affected by Crohn's disease (lanes 1 and 2) possessed three bands (a, b and c), whereas all other RNA samples showed only two bands (a and b; FIG. 2).

The present strategy is not restricted to polyadenylated mRNAs, this may be considered as an advantage. An additional advantage is that when the goal of a molecular marker is reached for one pathological state, the cDNA pools are available for the analysis of other diseases, for example ulcerative colitis in the present study. Following the identification of potential markers from genetic expression, further PCR products identified as being selectively expressed can then be easily cloned, sequenced, and Northern blotted so as to verify the expression patterns. Thus, it is possible to envisage the development of clinical tools based on this methodology, and to initiate an evaluation of many samples. This methodology includes several helpful and even innovative variations into the RNA fingerprinting approach.

The present invention will be more readily understood by referring to the following examples which are given to illustrate the invention rather than to limit its scope.

EXAMPLE I

Identification of a Crohn's disease specific transcript possessing potential diagnostic marker Using the procedure of the present invention, identified, cloned and sequenced a 1065 basepairs PCR-product associated with the inflammation occurring in CD specimens. Northern blot hybridizations showed that this novel sequence originates from a unique RNA species of 3.1 kilobases. Dot-blot hybridizations clearly demonstrated that this RNA species was specific to the CD specimens. Moreover, the abundance of this transcript seemed to correlate with the severity of the CD inflammation. Finally, the detection of this RNA species was also performed in visually normal areas from CD specimens suggesting that it appears either early during the disease or at least before severe manifestations.

We report here the finding of a 3.1 kb RNA species that permits to discriminate CD manifestations. Although further clinical work is required, this transcript appears to have definite potential as a diagnostic marker.

SPECIMENS AND METHODS

Patients, tissues and RNA extraction

This study was approved by the ethical committee of the Centre de Recherche Clinique de l'Universite de Sherbrooke. Thirty-eight tissue specimens of intestinal surgical resections from thirty-four patients with active CD, UC, diverticulitis, familial polyposis or adenocarcinoma were obtained. These samples were washed with saline solution. Small sections from severely inflamed, less inflamed or nearby visually uninflamed areas were isolated and rapidly snap-frozen in liquid nitrogen prior to storage at −70° C. If multiple specimens were taken from one patient, they were taken from areas with different degrees of inflammation. Sections from the same areas were fixed for both histopathological analysis and confirmation of the clinical diagnosis. Total RNA was extracted from the frozen tissues using guanidinium thiocyanate (GITC; TRIZOL™ Reagent, Gibco-BRL) (Chomczynski P et al., *Anal. Biochem.*, 1987; 162:156–159), and stored at −70° C., quantified bu UV spectroscopy, and its quality verified by 1% agarose gel electrophoresis. Degraded RNA samples were rejected.

RNA arbitrarily primed PCR

RAP-PCR was performed as described previously on RNA populations isolated from different areas of surgically resected specimens. These specimens were obtained from patients with CD (two specimens from inflamed, one from less inflamed and one from non-inflamed areas). Similarly, samples from inflamed areas of one UC, one familial polyposis and two diverticulitis were chosen as control of inflammation, while two samples from altered areas of adenocarcinoma were chosen as controls of proliferation.

The AP-PCR was performed with a primer, which served as both sense and antisense primer, 5'GCTGTTTCCTTC-CCCGTC 3'(SEQ IF NO:1).

PCR-product cloning and sequencing

One PCR-product (1065 base pair (bp)) appeared specific to the inflamed CD specimens. The gel slice containing this band was isolated and the DNA extracted, ethanol precipitated and washed, and finally dried. This DNA fragment was cloned by taking advantage of the property of Taq DNA polymerase to add an adenosine at the 3' ends of the PCR products. Consequently, the PCR amplified fragment was easily ligated in "sticky end" fashion to a linearized vector pCR II possessing an extra thymidine residue at each 5' ends, the manufacturer (TA cloning kit, InvitroGen). The resulting clone (pCD1) was sequenced in both directions by the dideoxyribonucleotides chain termination method using the T7 sequencing kit (Pharmacia).

Northern and dot-blot hybridizations

Northern and dot-blot hybridizations were performed according to the general procedure described previously (Sambrook J, Fritsch EF, Maniatis T. Analysis of RNA. In: *Molecular cloning-A laboratory manual,* 2nd edition. Cold Spring Harbor, Cold Spring Harbor Laboratory Press, 1989: 7.37–7.52). In both cases, the probe was prepared from the pCD1 clone described above. For the Northern blot hybridizations, both sense and antisense riboprobes were prepared by in vitro transcription of linearized vector Sp6 or T7 RNA polymerase in the presence of [α32P]UTP. RNA isolated from different resected tissues were normalized for their 18S and 28S rRNA concentrations. RNA samples (20 μg) were denatured in the presence of glyoxal/DMSO, fractionated by 1% agarose gel electrophoresis and transferred overnight to nylon filters (Hybond N+; Amersham). The filters were pre-hybridized at 65° C. for 2 hours and hybridized at 65° C. overnight (~16 hours). After hybridization, the filters were successively washed twice in 2X SSC (20X SSC is 3 M sodium chloride, 0.33 M sodium citrate-NaOH pH 7.0) for 5 minutes at room temperature, once in 2X SSC-1% sodium dodecylsulfate (SDS) for 30 minutes at 65° C., once in 0,1X SSC-0.5% SDS for 30 minutes at 65° C., and finally in 0.1X SSC for 30 minutes at room temperature. The filters were then analyzed by either autoradiogram or PhosphorImager (Molecular Dynamics). For the dot-blot hybridizations, the probe consisted of the 1065-bp insert isolated DNA from the pCD1 by enzymatic digestion of the EcoR I flanking the cloning site of the pCR vector. The gel-purified DNA insert was then labeled using the multiprime DNA labeling system (Amersham) in presence of [α32P]dCTP. The procedure was identical to the Northern hybridization except that RNA samples (10 μg) were applied to the filter under vacuum.

Results

We have applied the recently revised RAP-PCR procedure for identifying potential clinical markers to CD. Samples of UC, diverticulitis and familial polyposis were used as inflammatory controls, while adenocarcinoma samples served as proliferation control (see Methods). All of these samples were required in order to assure the identification of a CD specific marker, and to eliminate any markers for more general pathological manifestations (e.g. inflammation or proliferation). Furthermore, several CD samples from normal and inflamed areas were used to reduce the possibility of identifying a RNA molecule specific to a unique individual. In total, 10 quality controlled and quantity normalized RNA samples were selected. More than 20 oligonucleotides were tested as arbitrary PCR primers without producing a band unique to all CD inflamed samples. However, several bands were observed to be specific to either a particular individual, or to both CD and UC samples. These results illustrate the necessity of working with many samples, even if this creates handling difficulties.

An 18-mer oligonucleotide (5'GCTGTTTCCTTCCC-CGTC 3'SEQ ID NO:1) was observed to produce patterns that included a PCR product of 1065 bp which was specific to severely as well as less inflamed CD specimen. Consequently, this product was analyzed in greater detail.

The 1065-bp PCR product was gel-extracted and cloned into the pCR II vector (see Methods). The resulting construct was named pCD1, and its 1065-bp insert DNA was sequenced in both directions (FIG. 3A).

FIG. 3A illustrates the complete nucleotide sequence of the 1065 bp PCR-product. The underlined nucleotides at both ends correspond to the PCR primer used.

A BLAST search of nucleic acid databases did not reveal any significant homologies (Altschul SF et al., *J. Mol. Biol.,* 1990; 215:403–410). The sequence included several potential open reading frames; however, because it does not correspond to the complete RNA molecule (see below), the identification of a putative protein would be premature. A Northern blot hybridization using either sense or antisense radiolabeled riboprobe synthesized from pCD1 was performed with RNA isolated from different patients than the ones used for the RAP-PCR. Only one of the probes gave a signal, thereby permitting the identification of the polarity of the natural RNA species. A single band corresponding to a mRNA of ~3.1 kilobases (kb) was detected exclusively in lanes containing RNA populations isolated from CD inflamed areas (FIG. 3B, lanes 2 and 3).

FIG. 3B illustrates a Northern blot hybridization. Lane 1 is a CD sample from non-inflamed area, lanes 2 and 3 are CD samples from inflamed areas of two distinct patients, lane 4 is a sample from an adenocarcinoma, and lane 5 is 1 ng of pCD1 insert. The arrow indicates the 3.1 kb RNA species. The positions of single-stranded DNA molecular weight markers are indicated on the right.

While samples from both a normal area of a CD specimen and an inflamed area of an adenocarcinoma showed no hybridizing bands (FIG. 3B, lanes 1 and 4). These results support the conclusion that the RAPPCR 1065-bp product as set forth in SEQ ID NO:2 is unique to the inflamed tissues of CD patients.

The detection of a single RNA species using this 1065-bp fragment (as set forth in SEQ ID NO:2) as probe suggests the possibility of performing dot-blot hybridizations. This method allows the screening of a greater number of specimens, and therefore should provide an excellent preliminary evaluation of the discriminatory potential of an RNA species for CD. An example of a dot-blot is presented in FIG. 3C.

FIG. 3C illustrates an example of a dot-blot hybridization assay. Sample 1 is an inflamed UC specimen; samples 2–4 are typical CD specimens, sample 5 is the non-radioactive probe (as control), sample 6 is from an individual with an adenocarcinoma, sample 7 is from an individual with inflamed CD but in which some rejuvenation has been observed, and sample 8 is from the inflamed area from an individual with an undetermined IBD.

Clearly, a positive signal is detected only with samples from the inflamed areas of CD tissues (samples 2, 3, 4 and 7), and not in control samples (samples 1 and 7). Furthermore, it seems that the abundance of the RNA species in question correlates with the severity of the inflammation; the more severe the inflammation, the stronger the signal. For example, samples 2 and 4 were from severely inflamed areas of CD patients, while sample 3, which has a less intense signal, was from a less severely altered CD specimen. In addition, a CD case from which rejuvenation was observed produced a barely visible signal (sample 7). These results suggest that the 3.1 kb mRNA species is closely related to the severity of the CD inflammation.

Finally, a clinically and pathologically indeterminable IBD sample was analyzed (sample 8, FIG. 3C). The 3.1 kb RNA was detected, suggesting that the patient is suffering from CD. This result shows the potential of the 3.1 kb RNA species as a diagnostic marker for Crohn's disease.

The dot-blot experiments described above, as well as other similar experiments, are summarized in Table I.

TABLE I

Detection of the 3.1 kb RNA species in various specimens

| pathologic diagnostic | visual aspect of the specimens | n tested | 3.1 kb RNA detected in n |
|---|---|---|---|
| Crohn's disease (CD) | ++ | 8 | 8 |
|  | + | 5 | 5 |
|  | − | 4 | 1 |
| ulcerative colitis (UC) | ++ | 4 | 0 |
| diverticulitis | ++ | 3 | 0 |
| familial polyposis | ++ | 2 | 0 |
| adenocarcinoma | ++ | 4 | 0 |
|  | − | 1 | 0 |
| lymphoma | ++ | 2 | 0 |
|  | − | 1 | 0 |
| undetermined IBD | ++ | 4 | 1 |

++ = severely altered,
+ = altered,
− = not altered.
n = number of specimens
kb = kilobase Briefly, the 3.1 kb RNA was only detected in CD samples, and never in the samples from the various control diseases. In four cases, samples isolated from both the inflamed and visually normal areas of the same CD tissues were analyzed. In one of these cases, the 3.1 kb transcript was detected in normal areas.

A long time goal of the medical research community has been the development of a clinical molecular marker for Crohn's disease (CD). Our primary focus has been on identifying differences between the genetic expression patterns of CD and intestinal tissues affected by other pathologies. Using a refined RAP-PCR procedure convenient to study samples from pathological samples (e.g. inflamed tissues)⁻2, we detected a 1065-bp PCR product associated with the CD manifestations present in surgical specimens. The DNA sequence of this PCR product showed no significant homology with any of those present in the various nucleic acid data-bases. However, preliminary PCR amplifications of DNA isolated from individuals suffering from CD, UC or other relevant intestinal pathologies, indicate that this 1065-bp pair fragment is part of the genomic DNA isolated from all tested individuals. In contrast, Northern blot hybridizations show that this PCR product originates from a unique RNA species of 3.1 kb detected only in those patients suffering from CD.

Dot-blot hybridations have shown that the 3.1 kb RNA species permits the discrimination of CD alterations from those of other intestinal diseases since this RNA species was detectable in all CD specimens from inflamed areas while absent in all controls. Moreover, it was detected in a visually normal area from a CD specimen, although in lower amount. This latest result suggests that this RNA molecule appears either early during the disease or at least before severe manifestations. It seems that the 3.1 kb could be an interesting molecular marker, since such a marker seems to appear relatively early in CD development. However, it should be kept in mind that the sampling is relatively small and insufficient for a solid statistical analysis. Furthermore, the detection was performed on samples from patients living within a small geographic area. Therefore, additional worldwide trials are absolutely required in order to validate the use of this RNA species as a CD molecular marker. Furthermore, it would be interesting to verify the expression of the corresponding gene when CD occurs in other parts of the gastrointestinal tract.

In summary, a CD specific transcript possessing potential as a diagnostic marker was identified. In order to allow further development of this potential diagnostic tool, the gene as well as the transcript and any putative expression product have to be considered. Further clinical work is required to validate the worldwide use of this potential marker, which may also provide a new avenue for research into Crohn's disease.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A specific PCR primer for the diagnosis of Crohn's disease, said primer having a nucleic acid sequence as set forth in SEQ ID NO:1.

2. A method for the diagnosis of Crohn's disease in a patient; which comprises the step of;

a) subjecting a nucleic acid sequence obtained from a biological sample of said patient to at least one of the following to determine the presence of Crohn's disease marker:

i) hybridization of said nucleic acid sequence with a specific probe for the diagnosis of Crohn's disease said probe comprising a nucleic acid sequence as set forth in SEQ ID NO:2, or a fragment thereof having a minimum of 100 bp in length, for a time sufficient for hybridization of said to occur; and detection of hybridization of said nucleic acid sequence with said probe; or ii) amplification by RAP-PCR of said nucleic acid sequence of said biological sample using a specific PCR primer as set forth in SEQ ID NO:1 for the diagnosis of Crohn's disease, and detection of an amplified nucleic acid sequence, wherein detection of hybridization in step i) or detection of an amplified nucleic acid sequence in step ii) is indicative of Crohn's disease marker.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA to mRNA (xi) SEQUENCE DESCRIPTION: SEQ ID NO:1:

-continued

```
GCTGTTTCCT TCCCCGTC                                                           18

(2) INFORMATION FOR SEQ ID NO:2:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: Genomic RNA (xi) SEQUENCE DESCRIPTION: SEQ ID NO:2:

GCTGTTTCCT TCCCCGTCGT AAAGTCTAAG ACAAAAACTC ACACCTGGAC CAGGCTGACT    60

CCTGGTGTAA AGCAGGAAGA TGTGATGAAA ACTAGAGCCA GGAATGTCAA CTCGCACTTT    120

AGTCTGGGAT GCTTGTGTGG TCAGTTTCGC CCACAGAACC CCAAAGAAAT TACACTGAGG    180

GCTACGTCTG ACCCCTTTCC CCAGTCCCCA GGGTCACGGG GCAGAAACTT CTCTCCCACA    240

CACCAAGCCC CAGGCCAGGG CCCTGGGAAA CCTCCCATGT CCTCGTCCCA CCTGCCCCAT    300

GTGGTTGTAC TGTTTCTCCC ATATTAGAGA TGTACAGAAC CAAGACTCAG ACAAGGGAAA    360

TGCATCCAAT CCAAAGGCAC AGAAATGATG GTGGAGATGC AAGTGCTGCA TCCAGGTCTA    420

GCTGACTCAA AGCCCATGGG CTTTTTTCCA GTGTTTCTTT CTGCACTTCA CCAAAATTGG    480

GAGACTCCTG GTGATGGCAA GCTGACTGTC TCCTGCGGCG TTTTCATTGC GTCTGTCAAG    540

TTTCATTTCA GGGGATAGGG ATCGAGCAGC ACAGATTCGA AACTTCCCAA ATCTCCAATA    600

AAAACAGACA GAACAATGAG AAGGCAAAAC TAAACCCCTT AGACAACCTC TACAGCAAAT    660

GAGGTGACAA CGTGTCCCCA AACTACAAAT ACAATCAGGT GGGCGGAGGG CACCAAATAC    720

AAGTAACTGT GTGTCACCAG CATCTGTGTA GGGCACAGCA AGGGAAGCTC CGGGCTCTGG    780

CAGGCTGGAG ATCAGGGAAC AGCAAAGTAG CCAACAGATG CTCAGAGGCA AACATGACAA    840

ACCACAGGAC TGTGGCAGAA GCTGAGAGGA GTTTCTAACT AAAAGCAGGT GATGTCAAGA    900

AGTCTAGTCT AGGGTAGGCT GACCTCCATA GATTCTCCAG AATGAATGTC CAGGGCTTCC    960

TTCCAGCAGG GCCCTTGCTG ACAGCAGATT CAACACTGAG ACAAGAGGGA TGACAGAGAC    1020

AAAGAAGAGT GGACCAGATA ACAGGAGGAC GGGGAAGGAA ACAGC                   1065
```